US008722734B2

(12) United States Patent
Daifotis et al.

(10) Patent No.: US 8,722,734 B2
(45) Date of Patent: May 13, 2014

(54) COMPOSITION FOR INHIBITION OF CATHEPSIN K

(75) Inventors: Anastasia Daifotis, Westfield, NJ (US); Selwyn Aubrey Stoch, Short Hills, NJ (US); Basil Avery Ince, Westfield, NJ (US); Cameron Black, Baie d'Urfe (CA)

(73) Assignees: Merck Sharp & Dohme Corp., Rahway, NJ (US); Merck Canada Inc., Quebec (CA)

( * ) Notice: Subject to any disclaimer, the term of this patent is extended or adjusted under 35 U.S.C. 154(b) by 755 days.

(21) Appl. No.: 11/885,421

(22) PCT Filed: Feb. 24, 2006

(86) PCT No.: PCT/US2006/006622
§ 371 (c)(1),
(2), (4) Date: Aug. 29, 2007

(87) PCT Pub. No.: WO2007/046842
PCT Pub. Date: Apr. 26, 2007

(65) Prior Publication Data
US 2008/0255072 A1    Oct. 16, 2008

Related U.S. Application Data

(60) Provisional application No. 60/657,982, filed on Mar. 2, 2005.

(51) Int. Cl.
*A01N 37/34* (2006.01)

(52) U.S. Cl.
USPC .............................. 514/521; 514/357; 514/620

(58) Field of Classification Search
None
See application file for complete search history.

(56) References Cited

U.S. PATENT DOCUMENTS

| 6,432,931 B1 | 8/2002 | Reszka et al. |
| 2004/0235728 A1 | 11/2004 | Stoch et al. |

FOREIGN PATENT DOCUMENTS

| WO | WO03/075836 | 9/2003 |
| WO | WO2005/056529 | 6/2005 |
| WO | 2006/056047 A1 | 6/2006 |
| WO | 2006/076797 A1 | 7/2006 |
| WO | 2007/003056 A1 | 1/2007 |

OTHER PUBLICATIONS

Heaney et al. Am J Clin Nutr, 2003, 77, 204-210.*
Narang et al. Ind J Clin Biochem, 2004, 19, 111-113.*
Lark, MW et al., Bone, vol. 30, No. 5, pp. 746-753 (2002), "A potent small molecule, nonpeptide inhibitor of cathepsin K (SB 331750) prevents bone matrix resorption in the ovariectomized rat".
Rodan, GA et al., Science, vol. 289, No. 5484, pp. 1508-1514 (2000), "Therapeutic Approaches to Bone Diseases".
Stoch, S.A. et al., Clinical Pharmacology & Therapeutics,vol. 86, No. 2, Aug. 2009, pp. 175-182.
Supplementary European Search Report and Opinion, completed on Apr. 11, 2011, 9 pages.

* cited by examiner

*Primary Examiner* — Kyle Purdy
(74) *Attorney, Agent, or Firm* — Nicole M. Beeler; Catherine D. Fitch

(57) ABSTRACT

The present invention relates to the a method of inhibiting bone resorption in a mammal in need thereof with an oral pharmaceutical composition comprising a cathepsin K inhibitor, or a pharmaceutically acceptable salt thereof, or a mixture thereof, according to a continuous schedule having a dosage interval of once weekly, biweekly, twice monthly or once monthly.

21 Claims, No Drawings

COMPOSITION FOR INHIBITION OF CATHEPSIN K

PRIORITY CLAIM

This application is a §371 National Stage Application of PCT/US2006/006622, filed on Feb. 24, 2006, which claims priority from U.S. Provisional Application Ser. No. 60/657,982, filed on Mar. 2, 2005.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, hypercalcemia of malignancy, multiple myeloma, and metastatic bone disease. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Cysteine protease inhibitors such as E-64 (trans-epoxysuccinyl-L-leucylamide-(4-guanidino) butane) are known to be effective in inhibiting bone resorption. See Delaisse, J M et al., 1987, *Bone* 8:305-313, which is hereby incorporated by reference in its entirety. Recently, cathepsin K was cloned and found specifically expressed in osteoclasts See Tezuka, K et al., 1994, *J Biol Chem* 269:1106-1109; Shi, G P et al., 1995, *FEBS Lett* 357:129-134; Bromme, D and Okamoto, K, 1995, *Biol Chem Hoppe Seyler* 376:379-384; Bromme, D et al., 1996, *J Biol Chem* 271:2126-2132; Drake, F H et al., 1996, *J Biol Chem* 271:12511-12516, which are hereby incorporated by reference in their entirety. Concurrent to the cloning, the autosomal recessive disorder, pycnodysostosis, characterized by an osteopetrotic phenotype with a decrease in bone resorption, was mapped to mutations present in the cathepsin K gene. To date, all mutations identified in the cathepsin K gene are known to eliminate collagenase activity. See Gelb, B D et al., 1996, *Science* 273:1236-1238; Johnson, M R et al., 1996, *Genome Res* 6:1050-1055; Hou, W-S et al., 1999 *J. Clin. Invest.* 103, 731-738 which are hereby incorporated by reference in their entirety. Therefore, it appears that cathepsin K is involved in osteoclast mediated bone resorption.

Human type I collagen, the major collagen in bone is a good substrate for cathepsin K. See Kafienah, W, et al., 1998, *Biochem J* 331:727-732, which is hereby incorporated by reference in its entirety. In vitro experiments using antisense oligonucleotides to cathepsin K, have shown diminished bone resorption in vitro, which is probably due to a reduction in translation of cathepsin K mRNA. See Inui, T, et al., 1997, *J Biol Chem* 272:8109-8112, which is hereby incorporated by reference in its entirety. The crystal structure of cathepsin K has been resolved. See McGrath, M E, et al., 1997, *Nat Struct Biol* 4:105-109; Zhao, B, et al., 1997, *Nat Struct Biol* 4:109-11, which are hereby incorporated by reference in their entirety. Also, selective peptide based inhibitors of cathepsin K have been developed See Bromme, D, et al., 1996, *Biochem J* 315:85-89; Thompson, S K, et al., 1997, *Proc Natl Acad Sci USA* 94:14249-14254, which are hereby incorporated by reference in their entirety. Accordingly, inhibitors of cathepsin K can reduce bone resorption. Such inhibitors would be useful in treating disorders involving bone resorption, such as osteoporosis.

Weekly and monthly compositions of a cathepsin K inhibitor would provide therapeutic advantages over other therapies and would enhance convenience, patient compliance and patient satisfaction.

SUMMARY OF THE INVENTION

The present invention relates to an oral pharmaceutical composition comprising a cathepsin K inhibitor, or a pharmaceutically acceptable salt thereof, or a mixture thereof, adapted for inhibiting bone resorption according to a continuous schedule having a dosage interval of once weekly, biweekly, twice monthly or once monthly.

DETAILED DESCRIPTION OF THE INVENTION

The present invention relates to the use of a cathepsin K inhibitor, or a pharmaceutically acceptable salt thereof, or a mixture thereof, for the manufacture of a medicament, characterized by a single-dose $AUC_{0-168}$ of about 2.00-80.0 μM/hr and a $C_{min}$ of about 10 nM to about 200 nM, as an oral unit dose for inhibiting bone resorption in a mammal in need thereof according to a continuous schedule having a dosage interval of once weekly, biweekly, twice monthly or once monthly. The present invention also relates to a method of inhibiting bone resorption in mammal in need thereof by administering a cathepsin K inhibitor, or a salt thereof, or a mixture thereof, characterized by a single-dose $AUC_{0-168}$ of about 2.00-80.0 μM/hr and a $C_{min}$ of about 10 nM to about 200 nM, in an oral unit dose according to a continuous schedule having a dosage interval of once weekly, biweekly, twice monthly or once monthly.

In an embodiment of the invention, the mammal, specifically a human, is identified as suffering from or susceptible to upper gastrointestinal disorders. In a class of the embodiment, the upper gastrointestinal disorder is gastrointestinal reflux disease (GERD), esophagitis, dyspepsia (heartburn) or ulcers.

In an embodiment of the invention, the present invention relates to the use of about 2.5 mg to about 250 mg of a cathepsin K inhibitor according to Formula I:

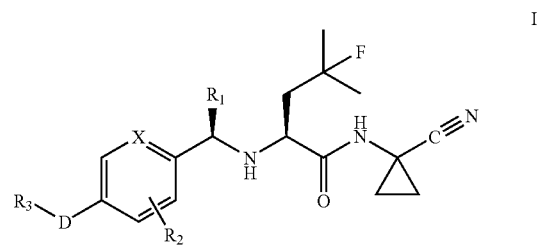

I wherein $R^1$ is $C_{1-3}$ alkyl which is substituted with two to seven halo;

$R^2$ is hydrogen or halo;

X is N or CH;

D is aryl or heteroaryl, wherein each said aryl or heteroaryl group, which may be monocyclic or bicyclic, is optionally substituted on either the carbon or the heteroatom with one to four substituents independently selected from methyl, $C_{1-6}$ haloalkyl, halo or —$SO_2R^4$;

$R^3$ is hydrogen, $C_{1-6}$ alkyl, $C_{2-6}$ alkynyl, halo, cyano, aryl, heteroaryl, $C_{3-8}$ cycloalkyl, heterocyclyl, —$OR^4$, —$C(O)N(R^5)(R^6)$, —$C(R^5)(R^6)OH$, —$C(R^5)(R^6)N(R^4)_2$, —$SO_mR^4$, —$SO_2N(R^4)(R^5)$, or —$SO_2N(R^5)C(O)(R^7)$; wherein said alkyl, alkynyl, aryl, heteroaryl, cycloalkyl and heterocyclyl groups are optionally substituted on either the carbon or the heteroatom with one to five substituents independently selected from $C_{1-6}$ alkyl or halo;

$R^4$ is hydrogen, $C_{1-6}$ alkyl, aryl, aryl($C_{1-4}$) alkyl, heteroaryl, heteroaryl($C_{1-4}$)alkyl, $C_{3-8}$ cycloalkyl, $C_{3-8}$ cycloalkyl ($C_{1-4}$)alkyl, or heterocyclyl($C_{1-4}$)alkyl; which are optionally substituted with one, two, or three substituents independently selected from halo, alkoxy or —$SO_2R^7$;

$R^5$ is hydrogen, $C_{1-6}$ alkyl, or $C_{1-6}$ haloalkyl;

$R^6$ is hydrogen, $C_{1-6}$ alkyl, or $C_{1-6}$ haloalkyl;

Or $R^5$ and $R^6$ can be taken together with the carbon or nitrogen atom between them to form a 3 to 6 membered ring;

$R^7$ is hydrogen or $C_{1-6}$ alkyl which is optionally substituted with one, two, or three substituents independently selected from halo or cyano;

m is an integer from zero to two;

or a salt, stereoisomer, N-oxide derivative, or a mixture thereof, for the manufacture of a medicament as an oral unit dose for inhibiting bone resorption in a mammal in need thereof according to a continuous schedule having a dosage interval of once weekly, biweekly, twice monthly or once monthly.

In an embodiment of the invention, the present invention relates to the use of about 2.5 mg to about 250 mg of a cathepsin K inhibitor according to Formula II:

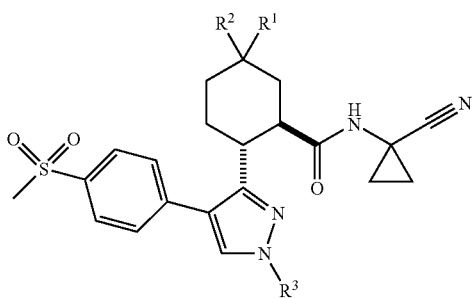

II wherein $R^1$ is halo;

$R^2$ is halo;

$R^3$ is hydrogen, $C_{1-6}$ alkyl, $C_{1-6}$ haloalkyl, $C_{3-6}$ cycloalkyl, aryl or heteroaryl;

or a salt, stereoisomer, N-oxide derivative, or a mixture thereof, for the manufacture of a medicament as an oral unit dose for inhibiting bone resorption in a mammal in need thereof according to a continuous schedule having a dosage interval of once weekly, biweekly, twice monthly or once monthly.

In an embodiment of the invention, the present invention relates to a method of inhibiting bone resorption in mammal in need thereof by administering a cathepsin K inhibitor according to formula I or II, or a pharmaceutically acceptable salt thereof, or a mixture thereof, characterized by a single-dose $AUC_{0-68}$ of about 2.00-80.0 μM/hr and a $C_{min}$ of about 10 nM to about 200 nM, in an oral unit dose according to a continuous schedule having a dosage interval of once weekly, biweekly, twice monthly or once monthly.

In a class of the embodiment, the present invention relates to the use of an oral pharmaceutical composition comprising about 2.5 mg to about 250 mg of a compound selected from the group consisting of:

$N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide;

$N^1$-(1-cyanocyclopropyl)-4-fluoro-$N^2$-{(1S)-2,2,2-trifluoro-1-[2'-methyl-4'-(methylsulfonyl)biphenyl-4-yl]ethyl}-L-leucinamide;

$N^2$-{(1S)-1-[4'-(aminosulfonyl)biphenyl-4-yl]-2,2,2-trifluoroethyl}-$N^1$-(1-cyanocyclopropyl)-4-fluoro-L-leucinamide;

$N^1$-(1-cyanocyclopropyl)-4-fluoro-$N^2$-[(1S)-2,2,2-trifluoro-1,4'-fluorobiphenyl-4-yl)ethyl]-L-leucinamide;

$N^2$-((1S)-1-1,4'-[1-(aminocarbonyl)cyclopropyl]biphenyl-4-yl)-2,2,2-trifluoroethyl)-$N^1$-(1-cyanocyclopropyl)-4-fluoro-L-leucinamide;

$N^1$-(1-cyanocyclopropyl)-4-fluoro-$N^2$-((1S)-2,2,2-trifluoro-1-{4-[4-(trifluoromethyl)-1,3-thiazol-2-yl]phenyl}ethyl)-L-leucinamide;

$N^2$-((1S)-1-{4'-[1-(aminocarbonyl)cyclopropyl]-2'-fluorobiphenyl-4-yl}-2,2,2-trifluoroethyl)-$N^1$-(1-cyanocyclopropyl)-4-fluoro-L-leucinamide;

$N^1$-(1-cyanocyclopropyl)-$N^2$-((1S)-1-{4'-[(1R)-2,2-difluoro-1-hydroxyethyl]biphenyl-4-yl}-2,2,2-trifluoroethyl)-4-fluoro-L-leucinamide;

$N^1$-(1-cyanocyclopropyl)-$N^2$-((1S)-1-{4'-[(1S)-2,2-difluoro-1-hydroxyethyl]biphenylyl-4-yl}-2,2,2-trifluoroethyl)-4-fluoro-L-leucinamide;

$N^1$-(1-cyanocyclopropyl)-4-fluoro-$N^2$-(1S)-2,2,2-trifluoro-1-(4-[5-methyl-6-(methylsulfonyl)pyridin-3-yl]phenyl)ethyl)-L-leucinamide;

$N^1$-(1-cyanocyclopropyl)-$N^2$-{(1S)-1-[4'-(1-cyanocyclopropyl)biphenyl-4-yl]-2,2,2-trifluoroethyl}-4-fluoro-L-leucinamide;

$N^2$-[(1S)-1-(4-{5-[1-(aminocarbonyl)cyclopropyl]-3-chloropyridin-2-yl}phenyl)-2,2,2-trifluoroethyl]-$N^1$-(1-cyanocyclopropyl)-4-fluoro-L-leucinamide;

$N^2$-[(1S)-1-(5-{4-[1-(aminocarbonyl)cyclopropyl]phenyl}pyridin-2-yl)-2,2,2-trifluoroethyl]-$N^1$-(1-cyanocyclopropyl)-4-fluoro-L-leucinamide;

$N^1$-(1-cyanocyclopropyl)-4-fluoro-$N^2$-((1S)-2,2,2-trifluoro-1-{5-[4-(methylsulfonyl)phenyl]pyridin-2-yl}ethyl)-L-leucinamide;

$N^1$-(1-cyanocyclopropyl)-4-fluoro-$N^2$-(1S)-2,2,2-trifluoro-1-[4'-(methylsulfinyl)-1,1'-biphenyl-4-yl]ethyl}-L-leucinamide;

$N^1$-(cyanocyclopropyl)-$N^2$-{(1S)-2,2-difluoro-1-[4'-(methylsulfonyl)biphenyl-4-yl]ethyl}-4-fluoro-L-leucinamide;

(1R,2R)—N-(1-cyanocyclopropyl)-5,5-difluoro-2-[4-[4-(methylsulfonyl)phenyl]-1H-pyrazol-3-yl]cyclohexanecarboxamide;

(1R,2R)—N-(1-cyanocyclopropyl)-5,5-difluoro-2-[4-[4-(methylsulfonyl)phenyl]-1-methyl-1H-pyrazol-3-yl]cyclohexanecarboxamide;

(1R,2R)—N-(1-cyanocyclopropyl)-5,5-dichloro-2-[4-[4-methylsulfonyl)phenyl]-1-methyl-1H-pyrazol-3-yl]cyclohexanecarboxamide;

(1R,2R)—N-(1-cyanocyclopropyl)-5,5-difluoro-2-[4-[4-(methylsulfonyl)phenyl]-1-(2,2,2-trifluoroethyl)-1H-pyrazol-3-yl]cyclohexanecarboxamide;

(1R,2R)—N-(1-cyanocyclopropyl)-5,5-dichloro-2-[4-[4-(methylsulfonyl)phenyl]-1-(2,2,2-trifluoroethyl)-1H-pyrazol-3-yl]cyclohexanecarboxamide;
and salts thereof.

In another embodiment of the invention, the present invention relates to a method of inhibiting bone resorption in a mammal in need thereof by administering a cathepsin K inhibitor selected from the compounds described above.

In a class of the embodiment of the invention, the cathepsin K inhibitor is $N^1$-(1-cyanocyclopropyl)-4-fluoro-$N^2$-{(1S)-2,2,2-trifluoro-1-[4'-methylsulfonyl)-1,1'-biphenyl-4-yl]ethyl}-L-leucinamide.

Methods of preparation for the above compounds are described in International Publications WO 03/075836, which published on Sep. 18, 2003 and WO 2005/000800, which published on Jan. 6, 2005.

In an embodiment of the invention, the present invention relates to the use of an oral pharmaceutical composition comprising about 2.5 mg to about 250 mg of a cathepsin K inhibitor and another agent selected from the group consisting of an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent; calcium; Vitamin D; a synthetic Vitamin D analogue; a Non-steroidal anti-inflammatory drug; a selective cyclooxygenase-2 inhibitor; an inhibitor of interleukin-1 beta; a LOX/COX inhibitor; a RANKL inhibitor; and the pharmaceutically acceptable salts and mixtures thereof. In a class of the embodiment, the agent is Vitamin D. In a subclass of the embodiment, the amount of Vitamin D is 2,800, IU, 5,600 IU, 7,000 IU, 8,400 IU, 11,200 IU, 14,000 IU, 16,800 IU or 19,600 IU. In a further subclass of the embodiment, the amount of Vitamin D to be dosed weekly is 2,800, IU, 5,600 IU, 7,000 IU, 8,400 IU or 11,200 IU. In a further subclass of the embodiment, the amount of Vitamin D to be dosed monthly is 11,200 IU, 14,000 IU, 15,400 IU, 16,800 IU or 19,600 IU.

It is understood that substituents and substitution patterns on the compounds described herein can be selected by one of ordinary skill in the art to provide compounds that are chemically and metabolically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having one to ten carbon atoms unless otherwise specified. For example, $C_1$-$C_{10}$, as in "$C_1$-$C_{10}$ alkyl" is defined to include groups having 1, 2, 3, 4, 5, 6, 7, 8, 9 or 10 carbons in a linear, branched, or cyclic arrangement. For example, "$C_1$-$C_{10}$ alkyl" specifically includes methyl, ethyl, propyl, butyl, pentyl, hexyl, heptyl, octyl, nonyl, decyl, and so on.

"Alkoxy" or "alkyloxy" represents an alkyl group as defined above, unless otherwise indicated, wherein said alkyl group is attached through an oxygen bridge. Examples of alkoxy include methoxy, ethoxy and the like.

The term "cycloalkyl" or "carbocycle" shall mean cyclic rings of alkanes of three to eight total carbon atoms, unless otherwise indicated, or any number within this range (i.e., cyclopropyl, cyclobutyl, cyclopentyl, cyclohexyl, cycloheptyl or cyclooctyl).

The term "alkynyl" refers to a hydrocarbon radical straight or branched, containing from 2 to 10 carbon atoms, unless otherwise specified, containing at least 1 carbon to carbon triple bond. Up to 3 carbon-carbon triple bonds may be present. Thus, "$C_2$-$C_6$ alkynyl" means an alkynyl radical having from 2 to 6 carbon atoms. Alkynyl groups include ethynyl, propynyl and butynyl. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon moiety of up to 12 atoms in each ring; wherein at least one ring is aromatic. Examples of such aryl groups include phenyl, naphthyl, tetrahydronaphthyl, indanyl, biphenyl, phenanthryl, anthryl or acenaphthyl. A preferable example of aryl is phenyl. In cases where the aryl substituent is bicyclic and one ring is non-aromatic, it is understood that attachment is via the aromatic ring.

The term "heteroaryl", as used herein, represents a stable monocyclic, bicyclic or tricyclic group of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "keto" means carbonyl (C=O).

The term "haloalkyl" means an alkyl radical as defined above, unless otherwise specified, that is substituted with one to five, preferably one to three halogen. Representative examples include, but are not limited to trifluoromethyl, dichloroethyl, and the like.

The term "arylalkyl" includes an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, and chlorophenylethyl. Examples of alkylaryl include, but are not limited to, toluoyl, ethylphenyl, and propylphenyl.

The term "heteroarylalkyl" as used herein, shall refer to a system that includes a heteroaryl portion, where heteroaryl is as defined above, and contains an alkyl portion. Examples of heteroarylalkyl include, but are not limited to, thienylmethyl, thienylethyl, thienylpropyl, pyridylmethyl, pyridylethyl and imidazoylmethyl.

The term "cycloalkylalkyl" includes an alkyl portion where alkyl is as defined above and also includes a cycloalkyl portion where cycloalkyl is as defined above. Examples of cycloalkylalkyl include, but are not limited to, cyclopropylmethyl, cyclopentylmethyl, cyclohexylmethyl, cyclopropylethyl, and the like.

The term "heterocyclylalkyl" as used herein, shall refer to a system that includes a heterocyclyl portion, where heterocyclyl is as defined above, and contains an alkyl portion. Examples of heterocyclylalkyl include, but are not limited to, oxiranyl, azetidinyl, pyrrolidinyl, piperidinyl, piperazinyl, and morpholinyl.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also emcompassed by this definition.

The cathepsin K inhibitors described herein also include N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The cathepsin K inhibitors described herein can be administered in such oral dosage forms as tablets, capsules (each of which includes sustained release or timed release formulations), pills, powders, granules, liquids, elixers, suspensions, syrups and emulsions.

The dosage regimen utilizing the cathepsin K inhibitors described herein is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

The present invention also encompasses a pharmaceutical composition useful in the treatment of osteoporosis or other bone disorders, comprising the administration of a therapeutically effective amount of the cathepsin K inhibitors described herein, with or without pharmaceutically acceptable carriers or diluents. Suitable compositions of this invention include aqueous solutions comprising compounds of this invention and pharmacologically acceptable carriers. An embodiment of the invention includes a pharmaceutical composition comprising about 2.5 mg to about 200 mg of a cathepsin K inhibitor selected from $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide;

$N^1$-(1-cyanocyclopropyl)-4-fluoro-$N^2$-{(1S)-2,2,2-trifluoro-1-[2'-methyl-4'-(methylsulfonyl)biphenyl-4-yl]ethyl}-L-leucinamide;

$N^2$-{(1S)-1-[4'-(aminosulfonyl)biphenyl)-4-yl]-2,2,2-trifluoroethyl}-$N^1$-(1-cyanocyclopropyl)-4-fluoro-L-leucinamide;

$N^1$-(1-cyanocyclopropyl)-4-fluoro-$N^2$-[(1S)-2,2,2-trifluoro-1-(4'-fluorobiphenyl-4-yl)ethyl]-L-leucinamide;

$N^2$-((1S)-1-{4'-[1-(aminocarbonyl)cyclopropyl]biphenyl-4-yl}-2,2,2-trifluoroethyl)-$N^1$-(1-cyanocyclopropyl)-4-fluoro-L-leucinamide;

$N^1$-(1-cyanocyclopropyl)-4-fluoro-$N^2$-((1S)-2,2,2-trifluoro-1-{4-[4-(trifluoromethyl)-1,3-thiazol-2-yl]phenyl}ethyl)-L-leucinamide;

$N^2$-((1S)-1-{4'-[1-(aminocarbonyl)cyclopropyl]-2'-fluorobiphenyl-4-yl}-2,2,2-trifluoroethyl)-$N^1$-(1-cyanocyclopropyl)-4-fluoro-L-leucinamide;

$N^1$-(1-cyanocyclopropyl)-$N^2$-((1S)-1-{4'-[(1R)-2,2-difluoro-1-hydroxyethyl]biphenyl-4-yl}-2,2,2-trifluoroethyl)-4-fluoro-L-leucinamide;

$N^1$-(1-cyanocyclopropyl)-$N^2$-((1S)-1-{4'-[(1S)-2,2-difluoro-1-hydroxyethyl]biphenyl-4-yl}-2,2,2-trifluoroethyl)-4-fluoro-L-leucinamide;

$N^1$-(1-cyanocyclopropyl)-4-fluoro-$N^2$-((1S)-2,2,2-trifluoro-1-{4-[5-methyl-6-(methylsulfonyl)pyridin-3-yl]phenyl}ethyl)-L-leucinamide;

$N^1$-(1-cyanocyclopropyl)-$N^2$-{(1S)-1-[4'-(1-cyanocyclopropyl)biphenyl-4-yl]-2,2,2-trifluoroethyl}-4-fluoro-L-leucinamide;

$N^2$-[(1S)-1-(4-{5-[1-(aminocarbonyl)cyclopropyl]-3-chloropyridin-2-yl}phenyl)-2,2,2-trifluoroethyl]-$N^1$-(1-cyanocyclopropyl)-4-fluoro-L-leucinamide;

$N^2$-[(1S)-1-(5-{4-[1-(aminocarbonyl)cyclopropyl]phenyl}pyridin-2-yl)-2,2,2-trifluoroethyl]-$N^1$-(1-cyanocyclopropyl)-4-fluoro-L-leucinamide;

$N^1$-(1-cyanocyclopropyl)-4-fluoro-$N^2$-((1S)-2,2,2-trifluoro-1-{5-[4-(methylsulfonyl)phenyl]pyridin-2-yl}ethyl)-L-leucinamide;

$N^1$-(1-cyanocyclopropyl)-4-fluoro-$N^2$-{(1S)-2,2,2-trifluoro-1-[4'-(methylsulfinyl)-1,1'-biphenyl-4-yl]ethyl}-L-leucinamide;

$N^1$-(1-cyanocyclopropyl)-$N^2$-{(1S)-2,2-difluoro-1-[4'-(methylsulfonyl)biphenyl-4-yl]ethyl}-4-fluoro-L-leucinamide;

(1R,2R)—N-(1-cyanocyclopropyl)-5,5-difluoro-2-[4-[4-(methylsulfonyl)phenyl]-1H-pyrazol-3-yl]cyclohexanecarboxamide;

(1R,2R)—N-(1-cyanocyclopropyl)-5,5-difluoro-2-[4-[4-(methylsulfonyl)phenyl]-1-methyl-1H-pyrazol-3-yl]cyclohexanecarboxamide;

(1R,2R)—N-(1-cyanocyclopropyl)-5,5-dichloro-2-[4-[4-(methylsulfonyl)phenyl]-methyl-1H-pyrazol-3-yl]cyclohexanecarboxamide;

(1R,2R)—N-(1-cyanocyclopropyl)-5,5-difluoro-2-[4-[4-(methylsulfonyl)phenyl]-1-(2,2,2-trifluoroethyl)-1H-pyrazol-3-yl]cyclohexanecarboxamide;

(1R,2R)—N-(1-cyanocyclopropyl)-5,5-dichloro-2-[4-[4-(methylsulfonyl)phenyl]-1-(2,2,2-trifluoroethyl)-1H-pyrazol-3-yl]cyclohexanecarboxamide;
or a salt thereof.

In a class of the embodiment, the cathepsin K inhibitor is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide or a salt thereof.

In one exemplary application, a suitable amount of compound is administered to a mammal undergoing treatment for a cathepsin dependent condition. Oral dosages of the present invention, when used for the indicated effects, will range between about 0.01 mg per kg of body weight per week (mg/kg/week) to about 10 mg/kg/week, preferably 0.1 to 10 mg/kg/week, and most preferably 0.1 to 5.0 mg/kg/week. For oral administration, the compositions are preferably provided in the form of tablets containing 2.5 mg, 3.5 mg, 5 mg, 10 mg, 20 mg, 25 mg, 35 mg, 40 mg, 50 mg, 80 mg, 100 mg and 200 mg of the active ingredient for the symptomatic adjustment of the dosage to the patient to be treated. A medicament typically contains from about 2.5 mg to about 200 mg of the active ingredient, specifically, 2.5 mg, 3.5 mg, 5 mg, 10 mg, 20 mg, 25 mg, 35 mg, 40 mg, 50 mg, 80 mg, 100 mg and 200 mg of active ingredient. Advantageously, the cathepsin K inhibitor may be administered in a single weekly dose. Alternatively, the cathepsin K inhibitor may be administered in a biweekly, twice monthly or monthly dose.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, polyethylene glycol, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The cathepsin K inhibitors described herein can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Cathepsin K inhibitors described herein may also be delivered by the use of monoclonal antibodies as individual carriers to which the compound molecules are coupled. The cathepsin K inhibitors described herein may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the cathepsin K inhibitors described herein may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The present invention also encompasses a kit adapted for a continuous dosing schedule of a cathepsin K inhibitor having a dosing periodicity of once weekly, biweekly, twice monthly or once monthly comprising a number of unit doses of a pharmaceutical composition comprising a cathepsin K inhibitor, pharmaceutically acceptable salts thereof, or a mixture thereof.

In an embodiment of the invention, the cathepsin K inhibitor is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide.

In a further embodiment of the invention, the kit is for weekly administration. In a class of the invention, the unit doses comprise from 2.5 mg to about 200 mg of the cathepsin K inhibitor. In a subclass of the invention, the unit doses comprise 2.5 mg, 3.5 mg, 5 mg, 10 mg, 20 mg, 25 mg, 35 mg, 40 mg, 50 mg, 80 mg, 100 mg or 200 mg of the cathepsin K inhibitor. In another class of the invention, the kit is adapted for twice-weekly dosing. In a class of the invention, the unit doses comprise from 2.5 mg to 50 mg of the cathepsin K inhibitor. In a subclass of the invention, the unit doses comprise from 2.5 mg to 25 mg of the cathepsin K inhibitor. In another class of the invention, the kit is adapted for biweekly or twice-monthly dosing. In a class of the invention, the unit doses comprise from 2.5 mg to 50 mg of the cathepsin K inhibitor. In a subclass of the invention, the unit doses comprise from 2.5 mg to 25 mg of the cathepsin K inhibitor.

In an embodiment of the invention, the kit is a blister pack. In a class of the invention, the kit further comprises a memory aid designating the days in the treatment schedule in which the dosages can be administered. In a subclass of the invention, the memory aid is a calendar insert.

In an embodiment of the invention, the kit is adapted for administration on the same day of each week. In a class of the invention, the kit is adapted for weekly administration every Sunday.

Another embodiment of the invention is a method of inhibiting bone loss in a mammal in need thereof, comprising administering to the mammal a therapeutically effective amount of any of the compounds or any of the pharmaceutical compositions described above. Another embodiment of the invention is a method of reducing bone loss in a mammal in need thereof, comprising administering to the mammal a therapeutically effective amount of any of the compounds or any of the pharmaceutical compositions described above. The utility of cathepsin K inhibitors in the inhibition of bone resorption is known in the literature, see Stroup, G B, Lark, M W, Veber, D F., Bhattacharrya, A, Blake, S, Dare, L C, Erhard, K F, Hoffman, S J, James, I E, Marquis, R W, Ru, Y, Vasko-Moser, J A, Smith, B R, Tomaszek, T and Gowen, M, "Potent and selective inhibition of human cathepsin K leads to inhibition of bone resorption in vivo in a nonhuman primate", J. Bone Miner. Res., 16:1739-1746; 2001; and Votta, B J, Levy, M A, Badger, A, Dodds, R A, James, I E, Thompson, S, Bossard, M J, Carr, T, Connor, J R, Tomaszek, T A, Szewczuk, L, Drake, F H, Veber, D, and Gowen, M, "Peptide aldehyde inhibitors of cathepsin K inhibit bone resorption both in vivo and in vitro", J. Bone Miner. Res. 12:1396-1406; 1997.

Another embodiment of the invention is a method of treating or preventing osteoporosis in a mammal in need thereof, comprising administering to the mammal a therapeutically effective amount of any of the compounds or any of the above pharmaceutical compositions described above. The utility of cathepsin K inhibitors in the treatment or prevention of osteoporosis is known in the literature, see Saftig, P, Hunziker, Wehmeyer, O, Jones, S, Boyde, A, Rommerskirch, W, Moritz, J D, Schu, P, and Vonfigura, K, "Impaired osteoclast bone resorption leads to osteopetrosis in cathepsin K-deficient mice", Proc. Natl. Acad. Sci. USA 95:13453-13458; 1998.

Another embodiment of the invention is a method of treating or preventing rheumatoid arthritic condition in a mammal in need thereof, comprising administering to the mammal a therapeutically effective amount of any of the compounds or any of the pharmaceutical compositions described above. It is known in the literature that progressive destruction of the periarticular bone is a major cause of joint dysfunction and disability in patients with rheumatoid arthritis (RA), see Goldring S R, "Pathogenesis of bone erosions in rheumatoid arthritis", Curr. Opin. Rheumatol. 2002; 14: 406-10. Analysis of joint tissues from patients with RA have provided evidence that cathepsin K positive osteoclasts are the cell types that mediate the focal bone resorption associated with rheumatoid synovial lesion, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74. In addition, generalized bone loss is a major cause of morbidity associated with severe RA. The frequency of hip and spinal fractures is substantially increased in patients with chronic RA, see Gould A, Sambrook, P, Devlin J et al, "Osteoclastic activation is the principal mechanism leading to secondary osteoporosis in rheumatoid arthritis", J. Rheumatol. 1998; 25: 1282-9. The utility of cathepsin K inhibitors in the treatment or prevention of resorption in subarticular bone and of generalized bone loss represent a rational approach for pharmacological intervention on the progression of rheumatoid arthritis.

Another embodiment of the invention is a method of treating or preventing the progression of osteoarthritis in a mammal in need thereof, comprising administering to the mammal a therapeutically effective amount of any of the compounds or any of the pharmaceutical compositions described above. It is known in the literature that osteoarthritis (OA) is accompanied with well-defined changes in the joints, including erosion of the articular cartilage surface, peri-articular endochondral ossification/osteophytosis, and subchondral bony sclerosis and cyst formation, see Oettmeier R, Abendroth, K, "Osteoarthritis and bone: osteologic types of osteoarthritis of the hip", Skeletal Radiol. 1989; 18: 165-74. Recently, the potential contribution of subchondral bone sclerosis to the initiation and progression of OA have been suggested. Stiffened subchondral bone as the joint responding to repetitive impulsive loading, is less able to attenuate and distribute forces through the joint, subjecting it to greater mechanical stress across the articular cartilage surface. This in turn accelerates cartilage wear and fibrillate, see Radin, E L and Rose R M, "Role of subchondral bone in the initiation and progression of cartilage damage", Clin. Orthop. 1986; 213: 34-40. Inhibition of excessive subarticular bone resorption by an anti-resorptive agent such as a cathepsin K inhibitor, will lead to inhibition of subchondral bone turnover, thus may have a favorable impact on OA progression.

In addition to the above hypothesis, cathepsin K protein expression was recently identified in synovial fibroblasts, macrophage-like cells, and chondrocytes from synovium and articular cartilage specimens derived from OA patients, see Hou, W-S, Li, W, Keyszer, G, Weber, E, Levy, R, Klein, M J, Gravallese, E M, Goldring, S R, Bromnae, D, "Comparison of Cathepsin K and S expression within the Rheumatoid and Osteoarthritic Synovium", Arthritis Rheumatism 2002; 46: 663-74; and Dodd, R A, Connor, J R, Drake, F H, Gowen, M, "Expression of Cathepsin K messenger RNA in giant cells and their precursors in human osteoarthritic synovial tissues", Arthritis Rheumatism 1999; 42: 1588-93; and Konttinen, Y T, Mandelin, J, Li, T-F, Salo, J, Lassus, J et al., "Acidic cysteine endoproteinase cathepsin K in the degeneration of the superficial articular hyaline cartilage in osteoarthritis", Arthritis Rheumatism 2002; 46: 953-60. These recent studies thus implicated the role of cathepsin K in the destruction of collagen type II in the articular cartilage associated with the progression of osteoarthritis. The utility of cathepsin K inhibitors in the treatment or prevention of osteoarthritis as described in this invention thus comprise of two different mechanisms, one is on the inhibition of osteoclast-driven subchondral bone turnover, and two is on the direct inhibition of collagen type II degeneration in the synovium and cartilage of patients with OA.

Another embodiment of the invention is a method of treating cancer in a mammal in need thereof, comprising administering to the mammal a therapeutically effective amount of any of the compounds or any of the pharmaceutical compositions described above. It is known in the literature that cathepsin K is expressed in human breast carcinoma, prostate cancer and chordoma and has matrix degrading capabilities, see Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma", Cancer Res 1997 Dec. 1; 57(23):5386-90; Brubaker K D, Vessella R L, True L D, Thomas R, Corey E "Cathepsin K mRNA and protein expression in prostate cancer progression", J Bone Miner Res 2003 18, 222-30; and Haeckel C, Krueger S, Kuester D, Ostertag H, Samii M, Buehling F, Broemme D, Czerniak B, Roessner A, "Expression of cathepsin K in chordoma", Hum Pathol 2000 July; 31(7):834-40.

Another embodiment of the invention is a method of treating atherosclerosis in a mammal in need thereof, comprising administering to the mammal a therapeutically effective amount of any of the compounds or any of the pharmaceutical compositions described above. It is known in the literature that cathepsin K is expressed in human atheroma and has significant elastase activity, see Sukhova G K, Shi G P, Simon D I, Chapman H A, Libby P, "Expression of the elastolytic cathepsins S and K in human atheroma and regulation of their production in smooth muscle cells", J Clin Invest 1998 August 102, 576-83.

Another embodiment of the invention is a method of treating obesity and obesity related conditions in a mammal in need thereof, comprising administering to the mammal a therapeutically effective amount of any of the compounds or any of the pharmaceutical compositions described above. It is known in the literature that cathepsin K mRNA is increased in adipose tissue in several mouse models of obesity. In lean and obese male humans, a significant correlation between cathepsin K gene expression in adipose tissue and body mass index is observed see Chiellini C, Costa M, Novelli S E, Amri E Z, Benzi L, Bertacca A, Cohen P, Del Prato S, Friedman J M, Maffei M, "Identification of cathepsin K as a novel marker of adiposity in white adipose tissue", Cell Physiol 2003, 195, 309-21. These data show that a relationship exists between cathepsin K and adipogenesis and obesity.

Another embodiment of the invention is a method of treating chronic obstructive pulmonary disease in a mammal in need thereof, comprising administering to the mammal a therapeutically effective amount of any of the compounds or any of the pharmaceutical compositions described above. It is known in the literature that cathepsin K plays a role in lung fibrosis, see Buhling, F, et al., "Pivotal role of cathepsin K in lung fibrosis", Am J Pathol. 2004 June; 164(6):2203-16.

Another embodiment of the invention is a method of treating parasitic infections in a mammal in need thereof, comprising administering to the mammal a therapeutically effective amount of any of the compounds or any of the pharmaceutical compositions described above. It is known in the literature that mammalian cathepsins are related to the papain-like cysteine proteases which play an important role in the life cycle of these parasites. Such parasites are involved in the diseases of malaria, American trypanosomiasis, African trypanosomiasis, leishmaniasis, giardiasis, trichomoniasis, amoebiasis, schistosomiasis, fascioliasis, paragonimiasis and intestinal roundworms, see Lecaille F, Kaleta J, Bromme D, "Human and parasitic papain-like cysteine proteases: their role in physiology and pathology and recent developments in inhibitor design", Chem Rev 2002 102, 4459-88.

Another embodiment of the invention is a method of treating severe acute respiratory syndrome (SARS) in a mammal in need thereof, comprising administering to the mammal a therapeutically effective amount of any of the compounds or any of the pharmaceutical compositions described above.

Another embodiment of the invention is a method of treating metastatic bone disease in a mammal in need thereof, comprising administering to the mammal a therapeutically effective amount of any of the compounds or any of the pharmaceutical compositions described above. It is known in the literature that osteoclasts are responsible for bone resorption and that bone destruction and hypercalcemia induced by metastatic tumors are carried out by osteoclasts. Accordingly, the inhibition of osteoclasts can prevent bone destruction and bone metastasis, see Miyamoto, T and Suda, T, "Differentiation and function of osteoclasts", Keio J Med 2003 March; 52(1):1-7.

Another embodiment of the invention is administering to a mammal a therapeutically effective amount of any of the compounds or any of the pharmaceutical compositions described above for the treatment of mammalian diseases associated with cathepsin S including Alzheimer's disease, atherosclerosis, chronic obstructive pulmonary disease, neuropathic pain, nociceptive pain, cancer and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. It is known in the literature that cathepsin S activity is associated with the above disease states, see Munger J S, Haass C, Lernere C A, Shi G P, Wong W S, Teplow D B, Selkoe D J, Chapman H A, "Lysosomal processing of amyloid precursor protein to A beta peptides: a distinct role for cathepsin S", Biochem J 1995 311, 299-305; Sukhova G K, Zhang Y, Pan J H, Wada Y, Yamamoto T, Naito M, Kodama T, Tsimikas S, Witztum J L, Lu M L, Sakara Y, Chin M T, Libby P, Shi G P, "Deficiency of cathepsin S reduces atherosclerosis in LDL receptor-deficient mice", J Clin Invest 2003 111, 897-906; Zheng T, Zhu Z, Wang Z, Horner R J, Ma B, Riese R J Jr, Chapman H A Jr, Shapiro S D, Elias J A, "Inducible targeting of IL-13 to the adult lung causes matrix metalloproteinase- and cathepsin-dependent emphysema", J Clin Invest 2000 106, 1081-93; Shi G P, Sukhova G K, Kuzuya M, Ye Q, Du J, Zhang Y, Pan J H, Lu M L, Cheng X W, Iguchi A, Perrey S, Lee A M, Chapman H A, Libby P, "Deficiency of the cysteine protease cathepsin S impairs microvessel growth", Circ Res 2003 92, 493-500; and Nakagawa T Y, Brissette W H, Lira P D, Griffiths R J, Petrushova N, Stock J, McNeish J D, Eastman S E, Howard E D, Clarke S R, Rosloniec E F, Elliott E A, Rudensky A Y, "Impaired invariant chain degradation and antigen presentation and diminished collagen-induced arthritis in cathepsin S null mice", Immunity 1999 10,207-17.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The cathepsin K inhibitors described herein can be used in combination with other agents useful for treating cathepsin-mediated conditions, including, but not limited to osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, obesity, atherosclerosis, chronic obstructive pulmonary disorder, hypercalcemia of malignancy or multiple myeloma. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the cathepsin K inhibitors described herein in combination with a second agent selected from: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; a Nonsteroidal anti-inflammatory drug; a selective cyclooxygenase-2 inhibitor; an inhibitor of interleukin-1 beta; a LOX/

COX inhibitor; a RANKL inhibitor; and the pharmaceutically acceptable salts and mixtures thereof. The scope of the invention also encompasses a method of inhibiting bone resorption with the cathepsin K inhibitors described herein in combination with a second agent selected from: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; a Nonsteroidal anti-inflammatory drug; a selective cyclooxygenase-2 inhibitor; an inhibitor of interleukin-1 beta; a LOX/COX inhibitor; a RANKL inhibitor; and the pharmaceutically acceptable salts and mixtures thereof.

The instant compounds are also useful in combination with known agents useful for treating or preventing osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis, obesity, chronic obstructive pulmonary disease, metastatic bone disease, hypercalcemia of malignancy or multiple myeloma. Combinations of the presently disclosed cathepsin K inhibitors with other agents useful for treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; calcium; Vitamin D or a synthetic Vitamin D analogue; a Nonsteroidal anti-inflammatory drug; a selective cyclooxygenase-2 inhibitor; an inhibitor of interleukin-1 beta; a LOX/COX inhibitor; RANKL inhibitor; and the pharmaceutically acceptable salts and mixtures thereof. A preferred combination is a compound of the present invention and an organic bisphosphonate. Another preferred combination is a compound of the present invention and an estrogen receptor modulator. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

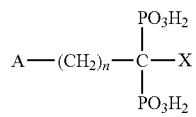

wherein n is an integer from 0 to 7 and wherein A and X are independently selected from the group consisting of H, OH, halogen, $NH_2$, SH, phenyl, $C_1$-$C_{30}$ alkyl, $C_3$-$C_{30}$ branched or cycloalkyl, bicyclic ring structure containing two or three N, $C_1$-$C_{30}$ substituted alkyl, $C_1$-$C_{10}$ alkyl substituted $NH_2$, $C_3$-$C_{10}$ branched or cycloalkyl substituted $NH_2$, $C_1$-$C_{10}$ dialkyl substituted $NH_2$, $C_1$-$C_{10}$ alkoxy, $C_1$-$C_{10}$ alkyl substituted thio, thiophenyl, halophenylthio, $C_1$-$C_{10}$ alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a $C_3$-$C_{10}$ ring.

In the foregoing chemical formula, the alkyl groups can be straight, branched, or cyclic, provided sufficient atoms are selected for the chemical formula. The $C_1$-$C_{30}$ substituted alkyl can include a wide variety of substituents, nonlimiting examples which include those selected from the group consisting of phenyl, pyridyl, furanyl, pyrrolidinyl, imidazonyl, $NH_2$, $C_1$-$C_{10}$ alkyl or dialkyl substituted $NH_2$, OH, SH, and $C_1$-$C_{10}$ alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-$C_1$-$C_{10}$-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronate, which is also known as alendronic acid, 4-amino-1-hydroxybutylidene-1,1-bisphosphonic acid, alendronate sodium or alendronate monosodium trihydrate, 4-amino-1-hydroxybutylidene-1,1-bisphospbonic acid monosodium trihydrate.

Alendronate is described in U.S. Pat. Nos. 4,922,007, to Kieczykowski et al., issued May 1, 1990; 5,019,651, to Kieczykowski et al., issued May 28, 1991; 5,510,517, to Dauer et al., issued Apr. 23, 1996; 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 µg/kg body weight and preferably about 10 to about 2000 µg/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week.

"Selective estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

An "estrogen receptor beta modulator" is a compound that selectively agonizes or antagonizes estrogen receptor beta (ERβ). Agonizing E Rβ increases transcription of the tryptophan hydroxylase gene (TPH, the key enzyme in serotonin synthesis) via an ERβ mediated event. Examples of estrogen receptor beta agonists can be found in PCT International publication WO 01/82923, which published on Nov. 8, 2001, and WO 02/41835, which published on May 20, 2002, both of which are hereby incorporated by reference in their entirety.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See Farina, C et al., "Selective inhibitors of the osteoclast vacuolar proton ATPase as novel bone antiresorptive agents", DDT, 4: 163-172 (1999), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885, 314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention. An illustration of the lactone portion and its corresponding open-acid form is shown below as structures I and II.

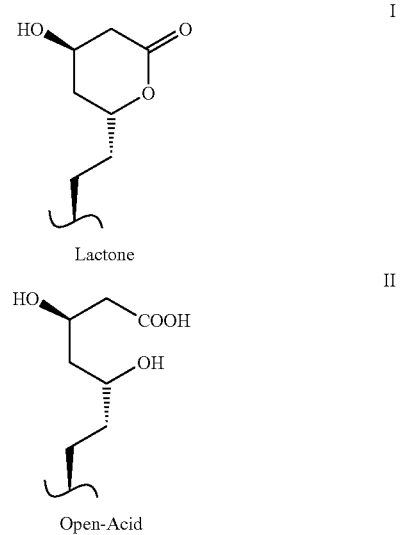

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylsulfate, mucate, napsylate, nitrate, oleate, oxalate, pamoate, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\gamma 5$ integrin, to compounds which antagonize, inhibit or counteract binding of a physiological ligand to both the $\alpha_v\beta_3$ integrin and the $\alpha_v\gamma_5$ integrin, and to compounds which antagonize, inhibit or counteract the activity of the particular integrin(s) expressed on capillary endothelial cells. The term also refers to antagonists of the $\alpha_v\beta_6$, $\alpha_v\gamma_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\gamma_3$, $\alpha_v\beta_3$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591-1596 (1999) have observed synergistic effects between an antiangiogenic $\alpha_v$ integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The $\alpha$ and $\beta$ integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\gamma_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to Dempster, D W et al., "Anabolic actions of parathyroid hormone on bone", Endocr Rev 14: 690-709 (1993). Studies have demonstrated the clinical benefits of parathyroid hormone in stimulating bone formation and thereby increasing bone mass and strength. Results were reported by Neer, R M et al., New Eng J Med 344 1434-1441 (2001).

In addition, parathyroid hormone-related protein fragments or analogues, such as PTHrP-(1-36) have demonstrated potent anticalciuric effects [see Syed M A et al., "Parathyroid hormone-related protein-(1-36) stimulates renal tubular calcium re-absorption in normal human volunteers: implications for the pathogenesis of humoral hypercalcemia of malignancy", JCEM 86: 1525-1531 (2001)] and may also have potential as anabolic agents for treating osteoporosis.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: 1α-hydroxy vitamin D; 25-hydroxy vitamin D, and 1α,25-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further hydroxylated in the kidney by cytochrome P450-monooxygenase, 25 (OH) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be responsible for the effects of vitamin D on calcium and bone metabolism. The 1,25-dihydroxy metabolite is the active hormone required to maintain calcium absorption and skeletal integrity. Calcium homeostasis is maintained by 1,25 dihydroxy vitamin D by inducing monocytic stem cells to differentiate into osteoclasts and by maintaining calcium in the normal range, which results in bone mineralization by the deposition of calcium hydroxyapatite onto the bone surface, see Holick, N R, "Vitamin D photobiology, metabolism, and clinical applications", In: DeGroot L, Besser H, Burger H G, et al., eds. Endocrinzology, $3^{rd}$ ed., 990-1013 (1995). However, elevated levels of 1α25-dihydroxy vitamin $D_3$ can result in an increase of calcium concentration in the blood and in the abnormal control of calcium concentration by bone metabolism, resulting in hypercalcemia. 1α,25-dihydroxy vitamin $D_3$ also indirectly regulates osteoclastic activity in bone metabolism and elevated levels may be expected to increase excessive bone resorption in osteoporosis.

In embodiments of the present invention, an appropriate amount of the vitamin D compound is chosen to provide adequate vitamin D nutrition during the dosing interval without interfering with the cathepsin K inhibitor's ability to obtain a bone resorption inhibiting effect. For oral compositions of the present invention comprising a cathepsin K inhibitor, and a vitamin D compound, an amount of the vitamin D compound comprises from about 100 IU to about 60,000 IU. Non-limiting examples of an oral amount of the vitamin D compound in embodiments of the present invention include, but are not limited to, dosages of 2,800, IU, 5,600 IU, 7,000 IU, 8,400 IU, 11,200 IU, 14,000 IU, 16,800 IU or 19,600 IU. Non-limiting examples of an oral amount of vitamin D for weekly dosing are 2,800, IU, 5,600 IU, 7,000 IU, 8,400 IU and 11,200 IU. Non-limiting examples of an oral amount of vitamin D for monthly dosing are 11,200 IU, 14,000 IU, 15,400 IU, 16,800 IU and 19,600 IU.

"Synthetic vitamin D analogues" includes non-naturally occurring compounds that act like vitamin D.

"Calcium" includes, but is not limited to, calcium carbonate, calcium citrate or any other compound containing elemental calcium. Calcium is essential to human health and is required for the structural integrity of the skeleton. The ionized fraction of blood calcium is physiologically important and is tightly maintained by both parathyroid hormone (PTH) and 1,25 dihydroxy Vitamin D. As such, decreases in blood calcium (or the mere insufficiency of dietary calcium) can readily affect PTH and 1,25 dihydroxy Vitamin D levels in such as way as to adversely affect skeletal health. Provision of supplemental calcium consequently tends to lower PTH levels, to diminish the removal of calcium from skeletal stores and, in so doing, to benefit skeletal health. Non-limiting examples of an oral amount of the calcium in embodiments of the present invention include, but are not limited to, dosages of 1200-1500 mgs of elemental calcium per day in divided doses.

"Nonsteroidal anti-inflammatory drugs" or NSAIDs, inhibit the metabolism of arachidonic acid to proinflammatory prostaglandins via cyclooxygenase (COX)-1 and COX-2. Nonlimiting examples of NSAIDs include: aspirin, ibuprofen, naproxen, diclofenac, etodolac, fenoporfen, flubiprofen, indomethacin, ketoprofen, ketorolac, meloxicam, nabumetone, oxaprozin, piroxicam, sulindac, tolmetin, diflunisal, meclofenarnate and phenylbutazone.

A "selective cyclooxygenase-2 inhibitor," or COX-2 inhibitor, refers to a type of nonsteroidal anti-inflammatory drug (NSAID), that inhibit the COX-2 coenzyme, which contributes to pain and inflammation in the body. Nonlimiting examples of COX-2 inhibitors include: celecoxib, etoricoxib, parecoxib, rofecoxib, valdecoxib and lumiracoxib.

An "inhibitor of interleukin-1 beta" or IL-1β refers to in inhibitors of IL-1, which is a soluble factor produced by monocytes, macrophages, and other cells which activates T-lymphocytes and potentiates their response to mitogens or antigens. Nonlimiting examples of IL-1B inhibitors include diacerein and rhein.

A "LOX/COX inhibitor" refers to an inhibitor or all three of the major enzymes involved in arachidonic acid pathway—namely, 5-LOX, COX-1 and COX-2. A nonlimiting example of a LOX/COX inhibitor is licofelone.

A "RANKL inhibitor" refers to an inhibitor of receptor activator NF-kB ligand (RANKL), which has previously been called osteoclast differentiation factor (ODF), osteoprotegerin ligand (OPGL) and TNF-related activation induced cytokine (TRANCE). RANKL is a key stimulator of osteoclast formation and maturation. A nonlimiting example or a RANKL inhibitor is AMG-162.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "AUC" or "Area Under the Curve" refers to the area defined by the plasma concentration-time curve over a given time period and represents the total exposure of the plasma to drug over a given time period. $AUC_{0-24}$ refers to the area under the concentration-time curve for the first 24 hours following administration of a compound. $AUC_{0-168}$ refers to the area under the concentration-time curve for the first 168 hours (one week) following administration of a drug.

The term "$C_{min}$" refers to the lowest concentration of drug circulating in plasma over a given time period. The time of minimal concentration is generally immediately prior to the administration of another dosage of the drug.

The terms "once weekly" and "once-weekly dosing," as used herein, means that a unit dosage, for example a unit dosage of a cathepsin K inhibitor, is administered once a week, i.e., once during a seven-day period, preferably on the same day of each week. In the once-weekly dosing regimen, the unit dosage is generally administered about every seven days. A non-limiting example of a once-weekly dosing regimen would entail the administration of a unit dosage of the cathepsin K inhibitor every Sunday. It is customarily recommended that a unit dosage for once-weekly administration is not administered on consecutive days, but the once-weekly dosing regimen can include a dosing regimen in which unit dosages are administered on two consecutive days falling within two different weekly periods.

By "biweekly" dosing is meant that a unit dosage of the cathepsin K inhibitor is administered once during a two week period, i.e. one time during a fourteen day period, preferably on the same day during each two week period. In the twice-weekly dosing regimen, each unit dosage is generally administered about every fourteen days. A nonlimiting example of a biweekly dosing regimen would entail the administration of a unit dosage of the cathepsin K inhibitor every other Sunday. It is preferred that the unit dosage is not administered on consecutive days, but the biweekly dosing regimen can include a dosing regimen in which the unit dosage is administered on two consecutive days within two different biweekly periods.

By "twice monthly" dosing is meant that a unit dosage of the cathepsin K inhibitor is administered twice, i.e. two times, during a monthly calendar period. With the twice monthly regimen, the doses are preferably given on the same two dates of each month. In the twice monthly dosing regimen, each unit dosage is generally administered about every fourteen to sixteen days. A nonlimiting example of a twice monthly dosing regimen would entail dosing on or about the first of the month and on or about the fifteenth, i.e. the midway point, of the month. It is preferred that the unit dosages are not administered on the same or consecutive days but the twice-monthly dosing regimen can include a dosing regimen in which the unit dosages are administered on two consecutive days within a monthly period, or different monthly periods. The twice monthly regimen is defined herein as being distinct from, and not encompassing, the biweekly dosing regimen because the two regimens have a different periodicity and result in the administration of different numbers of dosages over long periods of time. For example, over a one year period, a total of about twenty four dosages would be administered according to the twice monthly regimen (because there are twelve calendar months in a year), whereas a total of about twenty six dosages would be administered according to the biweekly dosing regimen (because there are about fifty-two weeks in a year).

The term "once monthly" is used in accordance with the generally accepted meaning as a measure of time amounting to approximately four weeks, approximately 30 days or 1/12 of a calendar year.

The term, "upper gastrointestinal disorders" refers to disorders associated with the upper gastrointestinal (GI) tract, including, but not limited to, gastrointestinal reflux disease (GERD), esophagitis, dyspepsia (heartburn) and ulcers.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. Bundgaard, H, Elsevier, 1985, which is incorporated by reference herein in its entirety. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "unit dose" as used herein describes a single unitary dose that is administered entirely at one time.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

These and other aspects of the invention will be apparent from the teachings contained herein.

The following examples are given for the purpose of illustrating the present invention and shall not be construed as limitations on the scope of the invention.

Pharmaceutical Compositions

For the following pharmaceutical compositions, $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide can be used as an example of a cathepsin K inhibitor.

| COMPOSITION 1 | |
|---|---|
| Ingredient | Percentage in Tablet |
| Cathepsin K inhibitor | 0.5-25% |
| Lactose | 30-50% |
| Microcrystalline Cellulose | 30-50% |
| Crosscamellose Sodium | 3-5% |
| Hydroxypropyl Cellose | 2-4% |
| Magnesium Stearate | 0.3-0.7% |

| COMPOSITION 2 | |
|---|---|
| Ingredient | Percentage in Tablet |
| Cathepsin K inhibitor | 0.5-25% |
| Lactose | 20-60% |
| Microcrystalline Cellulose | 20-60% |
| Crosscamellose Sodium | 2-6% |
| Hydroxypropyl Cellose | 1-5% |
| Magnesium Stearate | 0.2-0.8% |

| COMPOSITION 3 | |
|---|---|
| Ingredient | Percentage in Tablet |
| Cathepsin K inhibitor | 0.1-40% |
| Lactose | 10-70% |
| Microcrystalline Cellulose | 10-70% |
| Crosscamellose Sodium | 1-7% |

-continued

COMPOSITION 3

| Ingredient | Percentage in Tablet |
| --- | --- |
| Hydroxypropyl Cellose | 1-6% |
| Magnesium Stearate | 0.1-1% |

COMPOSITION 4

| Ingredient | Percentage in Tablet |
| --- | --- |
| Cathepsin K inhibitor | 0.5-25% |
| Lactose | 33.55-45.8% |
| Microcrystalline Cellulose | 33.55-45.8% |
| Crosscamellose Sodium | 4.0% |
| Hydroxypropyl Cellose | 3.0% |
| Magnesium Stearate | 0.5% |

What is claimed is:

1. A method of inhibiting bone resorption in a human in need thereof consisting of administering to the human 50 mg of $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide or a pharmaceutically acceptable salt thereof, as an oral unit dose according to a once weekly dosing regimen.

2. The method according to claim 1 where the oral unit dose is a tablet.

3. The method according to claim 1 for treating osteoporosis.

4. A method of treating osteoporosis in a human in need thereof consisting of administering to the human 50 mg of $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide as an oral unit dose according to a once weekly dosing regimen.

5. A method of treating osteoporosis in a human in need thereof consisting of administering to the human 50 mg of $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide and 5,600 IU of Vitamin D3 as an oral unit dose according to a once weekly dosing regimen.

6. The method according to claim 3 for treating osteoporosis in a postmenopausal woman.

7. The method according to claim 4 where the oral unit dose is a tablet.

8. The method according to claim 4 for treating osteoporosis in a postmenopausal woman.

9. The method according to claim 1 consisting of administering to the human 50 mg of $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide or a pharmaceutically acceptable salt thereof and Vitamin D, as an oral unit dose according to a once weekly dosing regimen.

10. The method according to claim 9 for treating osteoporosis.

11. The method according to claim 10 for treating osteoporosis in a postmenopausal woman.

12. A method of inhibiting bone resorption in a human in need thereof consisting of administering to the human 50 mg of $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide or a pharmaceutically acceptable salt thereof and Vitamin D, as an oral unit dose according to a once weekly dosing regimen.

13. The method according to claim 12 consisting of administering to the human 50 mg of $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide or a pharmaceutically acceptable salt thereof and Vitamin D, as an oral unit dose according to a once weekly dosing regimen.

14. The method according to claim 13 wherein the Vitamin D is Vitamin D3.

15. The method according to claim 14 wherein the amount of Vitamin D3 is from about 100 to 60,000 IU.

16. The method according to claim 15 wherein the amount of Vitamin D3 is 2,400 IU, 5,600 IU, 7,000 IU, 8,400 IU, 11,200 IU, 14,000 IU, 15,400 IU, 16,800 IU or 19,600 IU.

17. The method according to claim 16 wherein the amount of Vitamin D3 is 5,600 IU.

18. The method according to claim 16 wherein the amount of Vitamin D3 is 8,400 IU.

19. The method according to claim 16 wherein the amount of Vitamin D3 is 11,200 IU.

20. The method according to claim 13 for treating osteoporosis.

21. The method according to claim 20 for treating osteoporosis in a postmenopausal woman.

* * * * *

UNITED STATES PATENT AND TRADEMARK OFFICE
CERTIFICATE OF CORRECTION

PATENT NO. : 8,722,734 B2
APPLICATION NO. : 11/885421
DATED : May 13, 2014
INVENTOR(S) : Daifotis et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 995 days.

Signed and Sealed this
Twenty-eighth Day of July, 2015

Michelle K. Lee
*Director of the United States Patent and Trademark Office*